United States Patent [19]

Yuan et al.

[11] Patent Number: 5,760,234

[45] Date of Patent: Jun. 2, 1998

[54] CERTAIN 1-SUBSTITUTED AMINOMETHYL IMIDAZOLE AND PYRROLE DERIVATIVES: NOVEL DOPAMINE RECEPTOR SUBTYPE SPECIFIC LIGANDS

[75] Inventors: Jun Yuan, Clinton; Jan W. F. Wasley, Essex, both of Conn.

[73] Assignee: Neurogen Corporation, Branford, Conn.

[21] Appl. No.: 458,343

[22] Filed: Jun. 2, 1995

Related U.S. Application Data

[63] Continuation of Ser. No. 344,498, Nov. 23, 1994, Pat. No. 5,478,934.

[51] Int. Cl.$^6$ .................................................. C07D 401/06
[52] U.S. Cl. .................. 546/208; 546/210; 544/359; 544/372; 514/252; 514/326; 514/322
[58] Field of Search ........................... 546/208, 210

[56] References Cited

U.S. PATENT DOCUMENTS

| | | | |
|---|---|---|---|
| 4,829,065 | 5/1989 | Pascal et al. | 514/255 |
| 5,159,083 | 10/1992 | Thurkauf et al. | 548/335.5 |
| 5,428,164 | 6/1995 | Thurkauf et al. | 544/295 |

FOREIGN PATENT DOCUMENTS

| | | |
|---|---|---|
| 0 241 053 A1 | 10/1987 | European Pat. Off. . |
| 3627155 A1 | 2/1988 | Germany . |

OTHER PUBLICATIONS

Cerreto, F. et al. *Eur. J. Med. Chem.* 27, 701–708 (1992).

*Primary Examiner*—Mukund J. Shah
*Assistant Examiner*—King Lit Wong
*Attorney, Agent, or Firm*—McDonnell Boehnen Hulbert & Berghoff

[57] ABSTRACT

Disclosed are compounds of the formula:

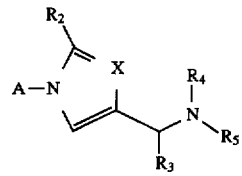

wherein:

A represents arylalkyl, aryl or heteroaryl; X is nitrogen or CH; and $R_2$, $R_3$, $R_4$ and $R_5$ represent organic or inorganic substituents;

and the pharmaceutically acceptable salts thereof; useful for treating disorders of the central nervous system.

8 Claims, 1 Drawing Sheet

Compound 1

Compound 2

Compound 3

Compound 7

Compound 8

5,760,234

CERTAIN 1-SUBSTITUTED AMINOMETHYL IMIDAZOLE AND PYRROLE DERIVATIVES: NOVEL DOPAMINE RECEPTOR SUBTYPE SPECIFIC LIGANDS

This is a continuation application of U.S. Ser. No. 08/344,498, filed Nov. 23, 1994, now U.S. Pat. No. 5,478,934.

BACKGROUND OF THE INVENTION

1. Field of the Invention

This invention relates to certain 1-substituted aminomethylimidazole and pyrrole derivatives which selectively bind to brain dopamine receptor subtypes. This invention also relates to pharmaceutical compositions comprising such compounds. It further relates to the use of such compounds in treating affective disorders such as schizophrenia and depression as well as certain movement disorders such as Parkinsonism.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive (disordered thought, hallucinations and delusions) and negative symptoms (social withdrawal and unresponsiveness). These disorders have an age onset of adolescence or early adulthood and persist for many years. The disorders tend to become more severe during the patient's lifetime and can result in prolonged institutionalization. In the U.S. today, approximately 40% of all hospitalized psychiatric patients suffer from schizophrenia.

During the 1950's physicians demonstrated that they could successfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in the brain. Several dopamine systems appear to exist in the brain and at least five classes of dopamine receptors appear to mediate the actions of this transmitter. These dopamine receptors differ in their pharmacological specificity and were originally classified upon these differences in the pharmacology of different chemical series. Butyrophenones, containing many potent antipsychotic drugs were quite weak at the dopamine receptor that activated adenylate cyclase (now known as the D1 dopamine receptor). In contrast, they labeled other dopamine receptors (called D2 receptors) in the subnanomolar range and a third type D3 in the nanomolar range. Two additional receptor subtypes have also been identified. D5 which is somewhat similar to D1 receptor type and D4 which is closely related to D3 and D2 receptor types. Phenothiazines possess nanomolar affinity for all three types of dopamine receptors. Other drugs have been developed with great specificity for the D1 subtype receptor and for the D2 subtype receptor.

Recently a new group of drugs (such as sulpiride and clozapine) have been developed with a lesser incidence of extrapyramidal side effects than classical neuroleptics. In addition, there is some indication that they may be more beneficial in treating negative symptoms in some patients. Since all D2 blockers do not possess a similar profile, hypotheses underlying the differences have been investigated. The major differences have been in the anticholinergic actions of the neuroleptics as well as the possibility that the dopamine receptors may differ in motor areas from those in the limbic areas thought to mediate the antipsychotic responses. The existence of the D3, D4, (Van Tol, et al, *Nature (London)* 1991, 350, 610) D5(Sunahara, et al, *Nature (London)* 1991, 350, 614) and other as yet undiscovered dopamine receptors may contribute to this profile. Some of the atypical compounds possess similar activity at both D2, D3 and D4 receptors. The examples of this patent fall into this general class of molecules.

Using molecular biological techniques it has been possible to clone cDNA's coding for each of the pharmacologically defined receptors. There are at least two forms of D1 which have been identified as D1 and D5, and two forms of D2, identified now as D2 and D4 dopamine receptors. In addition, there is at least one form of D3 dopamine receptor. Examples from the aminomethyl phenylimidazole series of this patent possess differential affinities for each receptor subtype.

German Patent Application DE. 3627155 describes the preparation of 1-aryimidazole-4-carboxamide derivatives.

The synthesis of a series of N-aryl pyrroles including 1 phenyl, 2,5-dimethyl-4-(4-methylpiperazine-1-ylmethyl) pyrroles and their antimicrobial activity has been described by F. Cerreto, M. Scalzo, A Villar in *Farmaco* (1993) 48(12) 1735–46 and *Euro J. Med. Chem.* (1992) 27(7), 701–8.

U.S. Pat. No. 5,159,083 discloses 4-Aminoalkyl 2-phenylimidazoles. U.S. Pat. No. 4,829,065 describes a series of 1-(Diphenylmethyl)-4-[(5 methyl-2-p-tolylimidazol-4-yl)methyl]piperazines. European Patent Application 87200296.9 discloses 2-Aryl-5(N-piperazinyl) methyl pyrroles.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidyl side effects associated with the use of conventional neuroleptic agents. Since particularly D3 and D4 receptor subtypes are concentrated in the limbic system (Taubes, *Science*, 1994, 265, 1034) which controls cognition and emotion, compounds which interact with these receptors also have utility in the treatment of cognitive disorders. Such disorders include cognitive deficits which are a significant component of the negative symptoms (social withdrawal and unresponsiveness) of schizophrenia. Other disorders involving memory impairment and attention deficit disorders may also be treated with the compounds of this invention that interact specifically with D3 and D4 receptors. Accordingly, broad embodiments of the invention is directed to compounds of Formulas I and II:

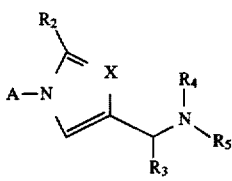

wherein:

A is arylalkyl, aryl or heteroaryl optionally substituted with up to 3 groups selected from the group consisting of halogen, trifluoromethyl, hydroxy, straight or branched chain lower alkyl having 1–6 carbon atoms or straight or branched chain lower alkoxy having 1–6 carbon atoms.

X is N or $CR_1$ where $R_1$ may be hydrogen, halogen straight or branched chain lower alkyl having 1–6 carbon atoms or phenyl substituted or unsubstituted.

$R_2$ is hydrogen, straight or branched chain, lower alkyl having 1–6 carbon atoms or phenyl substituted or unsubstituted;

$R_3$ is hydrogen or straight or branched chain lower alkyl having 1–6 carbon atoms, or $R_3$ and $R_4$ together may represent —$(CH_2)_{n_2}$— where $n_2$ is 3 or 4; and $R_4$ and $R_5$ are the same or different and represent hydrogen, straight or branched chain lower alkyl having 1–6 carbon atoms, aryl straight or branched chain lower alkyl having 1–6 carbon atoms; or $NR_4R_5$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms or;

$NR_4R_5$ represents

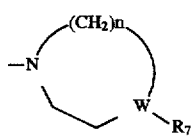

where
W is N or CH;

$R_7$ is hydrogen, arylalkyl, particularly benzyl, benzoyl, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; and n is 1, 2, or 3 when W is CH, or n is 2 or 3 when W is N; or $NR_4R_5$ represents

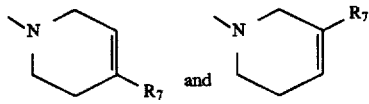

where $R_7$ is as defined above.

Alternatively, in Formula I, $R_2$ and A, where A is phenyl, may together form a tricyclic structure fused to the 5-membered nitrogen heterocycle to yield tetracyclic compounds of formula II;

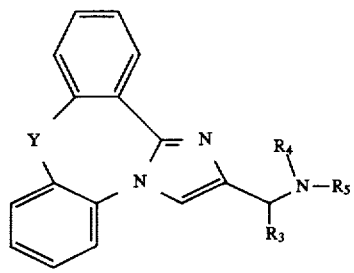

where

Y is oxygen, —$OCH_2$—, sulfur, —$SCH_2$—, or NR or —$NRCH_2$— where R represents hydrogen or alkyl; or Y is —CH=CH— or —$(CH_2)_m$— where m=0, 1, 2; and X, $R_3$, $R_4$, and $R_5$ are as defined above.

The interaction of the 1-substituted aminomethylimidazole and pyrrole derivatives of the invention with dopamine receptor subtypes results in the pharmacological activities of these compounds. These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Furthermore, compounds of this invention are useful in treating the extrapyramidyl side effects associated with the use of conventional neuroleptic agents.

DETAILED DESCRIPTION OF THE INVENTION

Figure 1A:
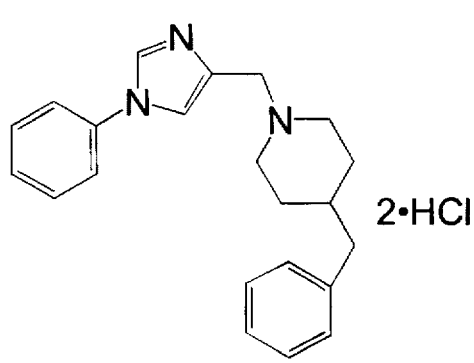
FIGS. 1A–1E show representative aminomethyl phenylimidazoles of the present invention.
Figure 1B:
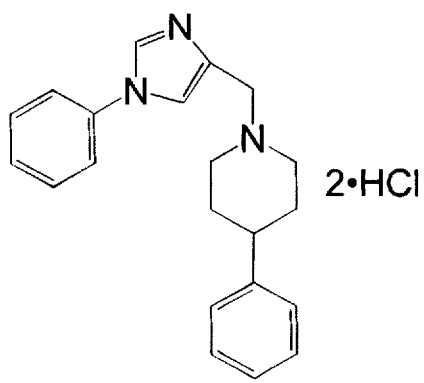
Figure 1C:
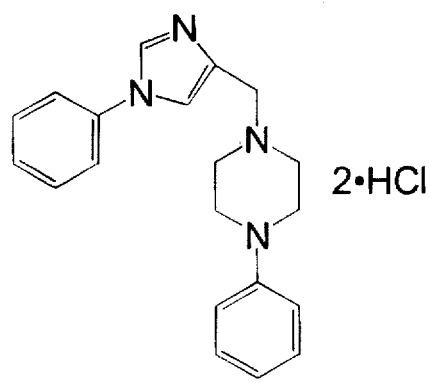
Figure 1D:
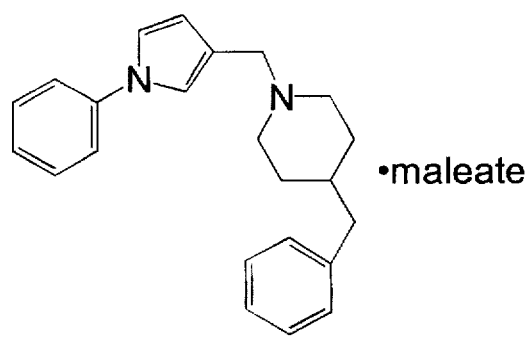
Figure 1E:
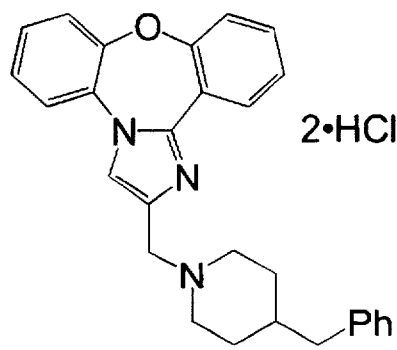

The novel compounds encompassed by the instant invention can be represented by general formulas I and II shown above.

Preferred compound of Formula I include those where A is phenyl, pyridyl, or naphthyl.

The present invention further encompasses compounds from Formula III:

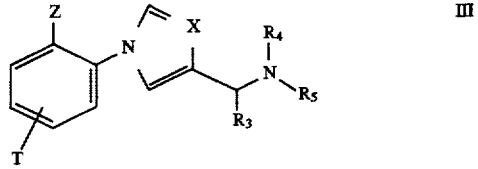

where

Z is hydrogen, halogen, trifluoromethyl, hydroxy, straight or branched chain lower alkyl having 1–6 carbon atoms, or straight or branched chain lower alkoxy having 1–6 carbon atoms;

T is hydrogen, halogen, hydroxy, straight or branched chain lower alkyl having 1–6 carbon atoms, straight or branched chain lower alkoxy having 1–6 carbon atoms; and X, $R_3$, $R_4$ and $R_5$ are as defined above for Formula I.

Alternatively, Z and T may form an additional ring as indicated by Formula IV and V

[Structure IV]

[Structure V]

where n=1–3; and X, R$_3$, R$_4$ and R$_5$ are as defined above for Formula I.

The present invention also encompasses compounds or Formula VI

[Structure VI]

where

Z is hydrogen, halogen, trifluoromethyl, straight or branched chain lower alkyl having 1–6 carbon atoms or straight or branched chain lower alkoxy having 1–6 carbon atoms; and X, R$_3$, R$_4$ and R$_5$ are as defined above for Formula I.

The invention further provides compounds of Formula VII

[Structure VII]

where Z and T are as defined above for Formula I; and W represents phenyl or phenylalkyl where the phenyl group is optionally mono- or disubstituted with halogen, alkyl, or alkoxy.

Preferred compounds of Formula VII are those where Z and T are hydrogen and W represents phenyl or benzyl.

The invention further provides compounds of Formula VIII

[Structure VIII]

where Z and T are as defined above for Formula I; and W represents phenyl, pyrimidinyl, pyridyl, or phenylalkyl where the phenyl group is optionally mono- or disubstituted with halogen, alkyl, or alkoxy.

Preferred compounds of Formula VIII are those where Z and T are hydrogen and W represents phenyl, pyrimidinyl, pyridyl, or benzyl.

The invention further provides compounds of Formula IX

[Structure IX]

where Z and T are as defined above for Formula I; V is nitrogen or CH; and W represents phenyl, pyrimidinyl, pyridyl, or phenylalkyl where the phenyl group is optionally mono- or disubstituted with halogen, alkyl, or alkoxy.

Preferred compounds of Formula IX are those where Z and T are hydrogen, V is CH; and W represents phenyl or benzyl. Other preferred compounds of Formula IX are those where Z and T are hydrogen, V is nitrogen and W represents phenyl, pyrimidinyl, pyridyl, or benzyl.

The invention also provides compounds of Formula X

[Structure X]

where W represents phenyl or phenylalkyl where the phenyl group is optionally mono- or disubstituted with halogen, alkyl, or alkoxy.

Preferred compounds of Formula X are those where W is phenyl or benzyl.

Representative compounds of the present invention, which are encompassed by Formula I, include, but are not limited to the compounds in FIG. I and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By alkyl and lower alkyl is meant straight and branched chain alkyl groups having from 1–6 carbon atoms.

By lower alkoxy and alkoxy is meant straight and branched chain alkoxy groups having from 1–6 carbon atoms.

By heteroaryl is meant 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By halogen is meant fluorine, chlorine, bromine and iodine.

By arylalkyl and aralkyl is meant the group —R—Ar where Ar is an aryl group and R is a straight or branched chain aliphatic group. Arylalkyl groups may optionally be substituted with, e.g., halogen, lower alkyl, lower alkoxy, lower alkylthio, trifluoromethyl, lower acyloxy, and hydroxy. Preferred arylalkyl groups in the above formulas where W is CH and $R_8$ represents arylalkyl are phenylalkyl groups where the alkyl portion is lower alkyl. A particularly preferred phenylalkyl group is benzyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

By cycloalkyl is meant cyclic hydrocarbons having from 3–8 carbon atoms. These cyclic hydrocarbon groups may be substituted with up to three substituents independently selected from hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$.

The pharmaceutical utility of compounds of this invention are indicated by the following assays for dopamine receptor subtype affinity.

Assay for D2 and D3 receptor binding activity

Striatial tissue is dissected from adult male Sprague Dawley rats or BHK 293 cells are harvested containing recombinantly produced D2 or D3 receptors. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.5 ml of tissue sample, 0.5 nM 3H-raclopride and the compound of interest in a total incubation of 1.0 ml. Nonspecific binding is defined as that binding found in the presence of 10-4 M dopamine; without further additions, nonspecific binding is less than 20% of total binding. The binding characteristics of examples of this patent are shown in Table 1 for Rat Striatal Homogenates.

TABLE I

| Compound Number[1] | $IC_{50}(\mu M)$ |
|---|---|
| 1 | 0.142 |
| 2 | 0.003 |
| 3 | 0.006 |
| 6 | 0.194 |

[1]Compound numbers relate to compounds shown in FIG. I.

Assay for D4 receptor binding activity

Clonal cell lines expressing the human dopamine D4 receptor subtype were harvested in PBS and the cells centrifuged and the pellets stored at −80° C. until used in the binding assay. The pellets were resuspended and the cells lysed at 4° C. in 50 mM Tris pH 7.4 buffer containing 120 mM NaCl, 2 mM EDTA and 5 mM $mMgCl_2$. The homogenate is centrifuged at 48000×g for 10 minutes at 4° C. The resulting pellet is resuspended in fresh buffer and centrifuged again. After resuspension of the pellet in fresh buffer at 100 ul aliquot removed for the protein determination. The remaining homogenate is centrifuged as above, the supernatant removed and the pellet stored at 4° C. until needed at which time it is resuspended to a final concentration of 625 ug/ml (250 ug per sample) with 50 mM Tris buffer (pH 7.4) and 120 mM NaCl just prior to use. Incubations were carried out for 60 minutes at 25° C. in the presence of 0.1 nM [$^3$H] YM-09151-2. The incubation was terminated by rapid filtration through Whatman GF/C filters and rinsed with 2×4 ml washes of chilled 50 mM (pH 7.4) and 120 mM NaCl. Nonspecific binding was determined with 1 μM spiperone and radioactivity determined by counting in an LKB beta counter. Binding parameters were determined by non-linear least squares regression analysis, from which the inhibition constant Ki could be calculated for each test compound. The binding characteristics of some examples of this patent are shown in Table 2 for the dopamine D4 binding assay. In general, compounds of the accompanying examples were tested in the above assay, and all were found to possess a Ki value for the displacement of [$^3$H] YM-09151-2 from the human dopamine D4 receptor subtype of below 500 mM. Some specific data is indicated in Table 2.

TABLE 2

| Compound Number[1] | Ki(μM) |
|---|---|
| 1 | 0.003 |
| 2 | 0.010 |
| 3 | 0.002 |
| 6 | 0.003 |

Compounds 1, 3, and 6 are particularly preferred embodiments of the present invention because of their potency in binding to dopamine receptor subtypes.

The compounds of general Formula I may be administered orally, topically, parenterally, by inhalation or spray or rectally in dosage unit formulations containing conventional non-toxic pharmaceutically acceptable carriers, adjutants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and if desired other active ingredients. The pharmaceutical compositions containing compounds of general formula I may be in a form suitable for oral use, for example as tablets, troches, lozenges, aqueous or oily suspensions, dispersible powders or granules, emulsion, hard or soft capsules or syrups or elixirs.

Compositions intended for oral use may be prepared according to any method known to the art for the manufacture of pharmaceutical compositions and such compositions may contain one or more agents, flavoring agents, coloring agents and preserving agents in order to provide pharmaceutically elegant and palatable preparations. Tablets contain the active ingredient in admixture with non-toxic pharmaceutically acceptable excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium sterate, stearic acid or talc, the tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example calcium carbonate, calcium posphate of kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene sterate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil for example liquid paraffin or mixtures of these. Suitable emulsifying agents may be naturally occurring gums, for example gum acacia or gum tragacanth, naturally occurring phospatides, for example soy bean, lecithin, and esters or partial esters derived from fatty acids and hexitol, anhydrides, for example sorbitan monoleate and condensation products of the said partial esters with ethylene oxide, for example polyoxyethylene sorbitan monoleate. The emulsions may also contain sweetening and flavoring agents.

Syrups and elixirs may be formulated with sweetening agents, for example, glycol, sorbitol or sucrose. Such formulations may also contain a demulcent, a preservative and flavoring and coloring agents. The pharmaceutical compositions may be in the form of a sterile injectable aqueous or oleaginous suspensions. This suspension may be formulated according to known art using those suitable dispersing or wetting agents and suspending agents which have been mentioned above. The sterile injectable preparation may also be sterile injectable solution or suspension in a nontoxic parentally acceptable diluent or solvent, for example as a solution of 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjutants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a singe dosage form will vary depending upon the host treated and the particular mode of administration. Dosage unit forms will generally contain between ca 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds if the present invention is given in Schemes I, II and III. Those having skill in the art will recognize that the starting materials may be varied and additional steps employed to produce compounds encompassed by the present invention.

Scheme I

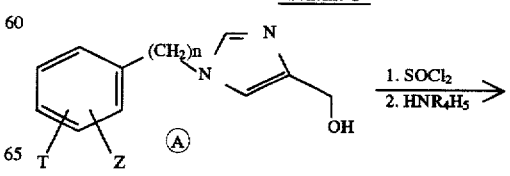

-continued
Scheme I

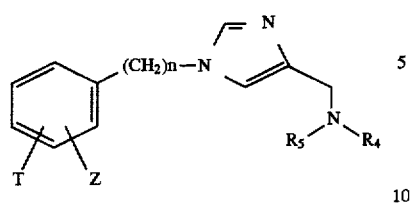

where n=0,1 or 2;

Z is hydrogen, halogen, hydroxy, trifluoromethyl, straight or branched chain lower alkyl having 1–6 carbon atoms or straight or branched chain lower alkoxy having 1–6 carbon atoms;

T is hydrogen, halogen, hydroxy, straight or branched chain lower alkyl having 1–6 carbon atoms or straight or branched chain lower alkoxy having 1–6 carbon atoms; or Z and T may together form an carbocyclic or heterocyclic ring system; and $R_4$ and $R_5$ are as defined as above for Formula I.

Representative illustrations of the starting materials A have been described by Antonini et al., Euro. J. Med. Chem., 19: 285 (1984).

Scheme II

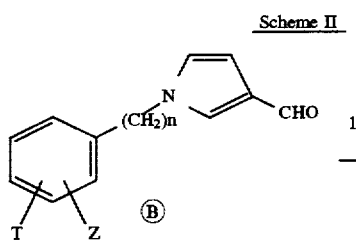

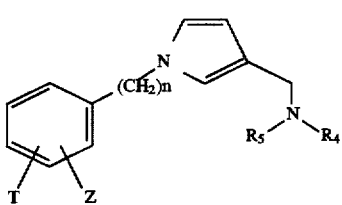

where all the substituents are as defined above.

Representative illustrations of the starting materials B are described in the literature. See, e.g., J. Wasley and K. Chan, Synth. Commun., 3 (4): 303–4 (1973).

Scheme III

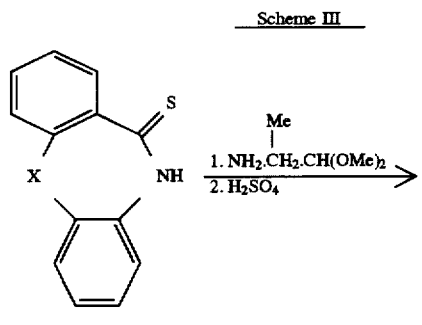

-continued
Scheme III

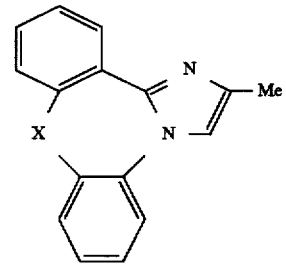

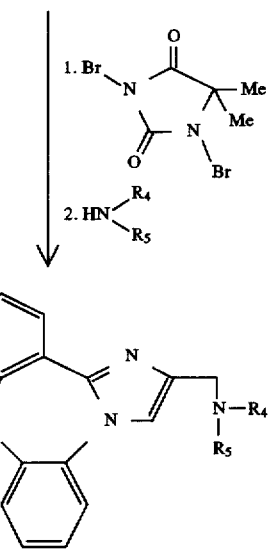

where all the substituents are as defined previously.

Representative illustrations of the starting materials C have been described by M. Gall and B. Kaundar, J. Org. Chem., 46: 1575 (1981).

The invention is illustrated further by the following examples which are not to be construed as limiting the invention in scope or spirit to the specific procedures and compounds described in them.

EXAMPLE I (Compound 1)

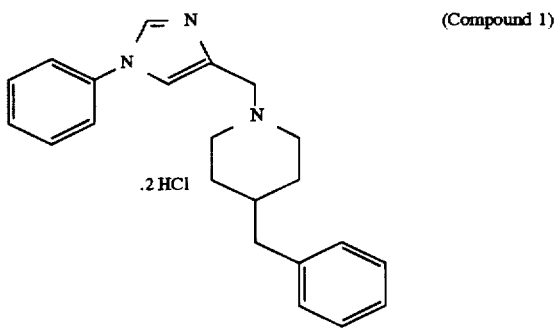

A solution of 50 mg of 4-hydroxymethyl-1-phenyl imidazole in 1 mL of thionyl chloride was heated at 60° C. for 1 hr. The excess thionyl chloride was removed by evaporation under reduced pressure. The residue was dissolved in 5 mL of chloroform and a mixture of 50 mg 4 benzylpiperidine and 0.5 mL N-ethyl-N,N diisopropylamine added. The reaction mixture was heated at 60° C. for 6 hr and then allowed to cool to room temperature. The reaction mixture then washed successively with 5 ml aliquots of 1N, NaOH and brine. The organic extracts were dried over anhydrous sodium sulfate and the solvent evaporated under reduced pressure to yield 1-phenyl-4[(4-benzyl-piperidin-1-yl)-methyl]imidazole, which after purification by chromatography on silica gel using 5% methanol in methylene chloride as elvent was converted to its dihydrochloride salt using ether/HCl. 1-phenyl-4-[benzyl-piperidin-1-y)methyl]imidazole dihydrochloride salt had a m.p. of 245°–8° C.

EXAMPLE II

The following compounds were prepared essentially according to the procedures described in Example I:

a) 1-Phenyl-4[(4-phenyl-piperidin-1-yl)methyl]imidazole dihydrochloride (compound 2) melting at 230°–233° C.

b) 1-Phenyl-4[(4-phenyl-piperazin-1-yl)methyl] imidazole dihydrochloride (compound 3) melting at 233°–237° C.

c) 1-Phenyl-4[(4-fluorobenzyl-piperidin-1-yl)methyl] imidazole dihydrochloride (compound 4) melting at 238°–241° C.

d) 1-Phenyl-4[(4-(4-fluoropyrimidin-2-yl)piperazin-1-yl) methyl]imidazole dihydrochloride (compound 5) melting at 233°–5° C.

e) 1-Phenyl-4[(4-(4-fluorophenyl)-piperazin-1-yl) methyl]imidazole dihydrochloride (compound 6) melting at 245°–7° C.

EXAMPLE III

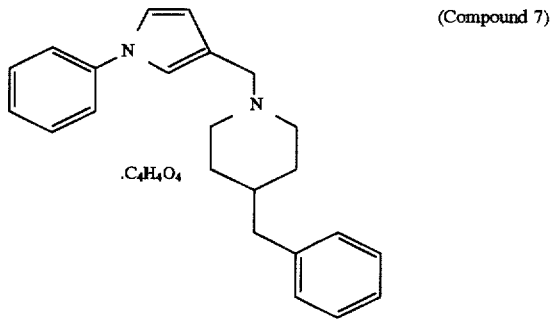

(Compound 7)

A mixture of 931 mg aniline and 2.0 g of 2,5-dimethoxy tetrahydrofuran-3-carboxaldehyde in 10 mL of acetic acid was heated at 90° C. for 2 hr. The acetic acid was removed by evaporation under reduced pressure and the residue was extracted into 50 mL of ethyl acetate. The organic extract was washed successively with 50 ml of 10% sodium bicarbonate and water, dried over anhydrous sodium sulfate and the solvent evaporated under reduced pressure to yield 1 g of 1 phenyl pyrrole-3-carboxaldehyde as a yellow oil which was used in the next step without further purification or characterization.

To a solution of 171 mg of 1-phenyl pyrrole-3-carboxaldehyde in 1 mL of methanol was added 525 mg of 4-benzylpiperidine, 175 mg of 4-benzylpiperidine.HCl and 63 mg of sodium cyanoborohydride. The reaction mixture was stirred overnight at room temperature under an atmosphere of nitrogen. The methanol was removed by evaporation under reduced pressure and the residue was extracted into 50 mL of ethyl acetate, then washed successively with 50 mL aliquots of 10% sodium hydroxide and water. The ethyl acetate extract was dried over anhydrous sodium sulfate and the solvent evaporated under reduced pressure to yield 1-phenyl-3[(4-benzylpiperidin-1-yl)methyl]pyrrole, which was purified by chromatography on silica gel using 5% methanol in dichloromethane as elvent. On evaporation of the solvent, the free base was dissolved in ethanol and treated with 1 equivalent of maleic acid. The 1-phenyl-3[(4-benzyl-piperidin-1-yl)methyl]pyrrole maleate salt (compound 7) had a melting point of 159°–161° C.

EXAMPLE IV

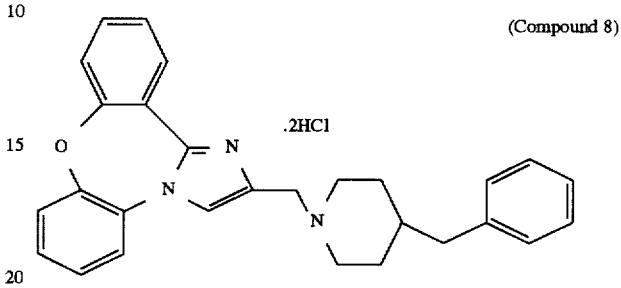

(Compound 8)

A mixture of 4 g of 10,11 dihydrobenz[b,f][1,4]oxazepin-11-thione and 4 g of 2-amino-1,1,dimethoxy propane in 40 mL of 1-butanol was heated at reflux temperature for 2 days. The solvent was then removed by evaporation under reduced pressure and the residue was dissolved in 10 mL conc. sulfuric acid and stirred at room temperature for 30 min. The reaction mixture was poured into 250 mL ice-water. The aqueous mixture was then basified with 3N sodium hydroxide and extracted with 2×100 mL of ethyl acetate. The combined organic extracts were washed with 2×100 mL brine, dried over anhydrous sodium sulfate and the solvent removed by evaporation under reduced pressure to yield 100 mg of 2-methyl-9H-dibenzo[b,f]imidazo[1,2d][1,4] oxazepine. This material was used in the next step without further purification or characterization.

To a suspension of 35 mg of 2-methyl-9H-dibenzo[b,f] imidazo[1,2d] [1,4]oxazepine in 3 mL of carbon tetrachloride was added 20 mg of 1,3-dibromo-5,5-dimethylhydantoin. The reaction mixture was stirred and irradiated with a 500 w lamp under an atmosphere of nitrogen. After 30 minutes, 100 mg of 4-benzyl-piperidine and 0.5 mL triethylamine was added to the mixture. The reaction mixture was stirred for 4 hr. at room temperature and then washed with 1N sodium hydroxide solution. The organic layer was dried over anhydrous sodium sulfate, and the solvent removed by evaporation under reduced pressure to yield 2[(4-benzyl-piperidin-1-yl)methyl-9H-dibenzo[b,f] imidazo[1,2d] [1,4]oxazepine. This material was purified by chromatography on silica gel using 5% methanol in dichlormethane as elvent and was treated with ether/HCl to yield 2[(4-benzyl-piperidin-1-yl)methyl]-9H-dibenzo[b,f] imidazo[1,2d[1,4]oxazepine dihydrochloride (compound 8) melting at 187°–190° C.

The disclosures in this application of all articles and references, including patents, are incorporated herein by reference.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A compound of the formula

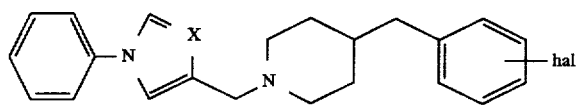

or the pharmaceutically acceptable salts thereof wherein:

X is N or $CR_1$ where $R_1$ is hydrogen, halogen, straight or branched chain lower alkyl having 1–6 carbon atoms or phenyl optionally substituted with halogen, or straight or branched chain lower alkyl having 1–6 carbon atoms; and hal represents halogen.

2. A compound according to claim 1, wherein hal is chloro.

3. A compound according to claim 1, wherein hal is fluoro.

4. A compound according to claim 1, wherein hal is bromo.

5. A compound according to claim 1 which is 1-phenyl-4[(4-(4-fluorobenzyl-piperidin-1-yl))methyl]imidazole dihydrochloride.

6. A compound according to claim 1 which is 1-phenyl-3[(4-benzyl-piperidin-1-yl)methyl] pyrrole maleate.

7. A compound according to claim 1 which is 1-phenyl-4[(4-(4-fluorobenzyl-piperidin-1-yl))methyl]imidazole.

8. A compound according to claim 1 which is 1-phenyl-3[(4-benzyl-piperidin-1-yl)methyl] pyrrole.

* * * * *